United States Patent [19]
Gross

[11] Patent Number: 5,385,563
[45] Date of Patent: Jan. 31, 1995

[54] URODYNAMIC CATHETER

[75] Inventor: James R. Gross, Wareham, Mass.

[73] Assignee: The Kendall Company, Mansfield, Mass.

[21] Appl. No.: 120,500

[22] Filed: Sep. 14, 1993

[51] Int. Cl.⁶ .......................... A61M 25/00; A61B 5/00
[52] U.S. Cl. ..................... 604/284; 128/748; 604/264
[58] Field of Search ............... 604/264, 280, 284, 100, 604/117; 128/748

[56]  References Cited
U.S. PATENT DOCUMENTS

| | | | |
|---|---|---|---|
| 4,538,621 | 9/1985 | Jarczyn | 128/748 |
| 5,090,959 | 2/1992 | Samson et al. | 604/96 |
| 5,108,364 | 4/1992 | Takezawa et al. | 128/748 |

Primary Examiner—John G. Weiss
Attorney, Agent, or Firm—Alvin Isaacs

[57] ABSTRACT

Disclosed is a urodynamic catheter having a fill lumen for filling the bladder with liquid; at least a first pressure-sensing lumen having an opening adapted for being positioned within the bladder for obtaining pressure readings of the bladder; and preferably also a second pressure-sensing lumen having an opening adapted for being positioned within the urethra while the opening of the first pressure-sensing lumen is within the bladder, the opening in the urethra being for obtaining pressure readings of the urethra.

Each pressure-sensing lumen has a radio-opaque element fixedly seated therewithin in close proximity to and distal to the opening in the lumen for determining proper placement of the catheter within the patient.

6 Claims, 2 Drawing Sheets

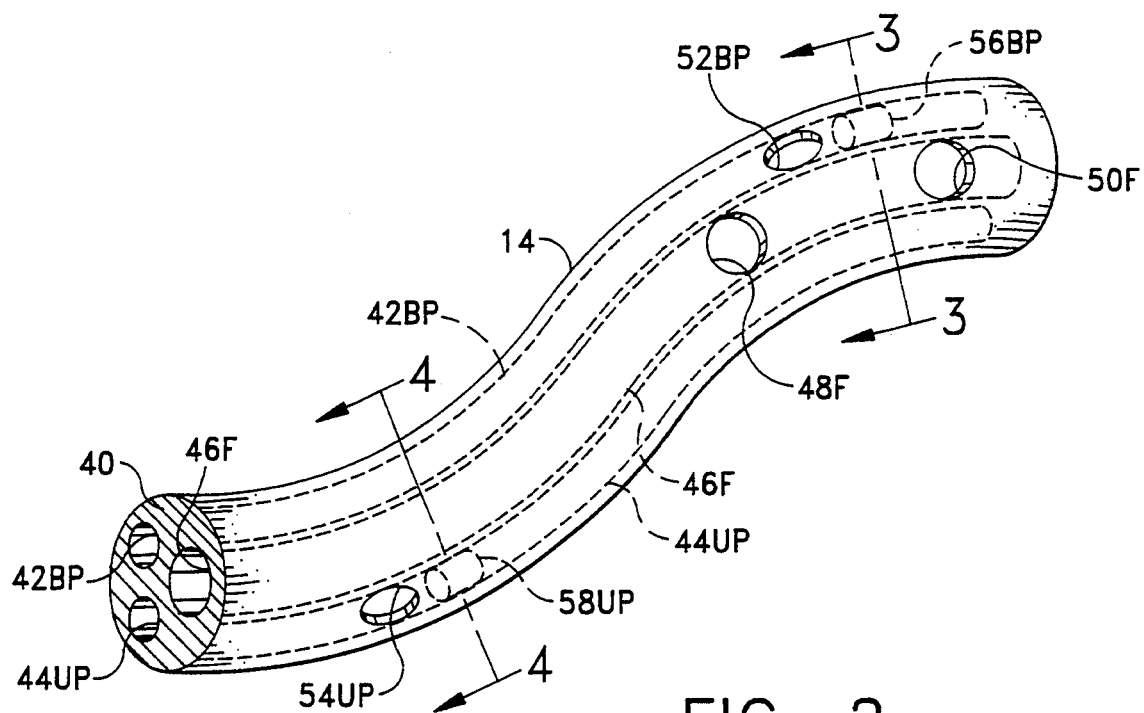
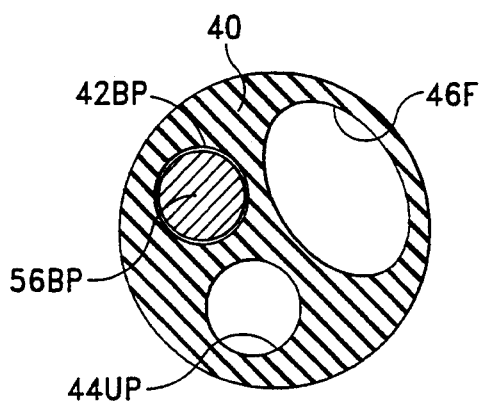
FIG. 3
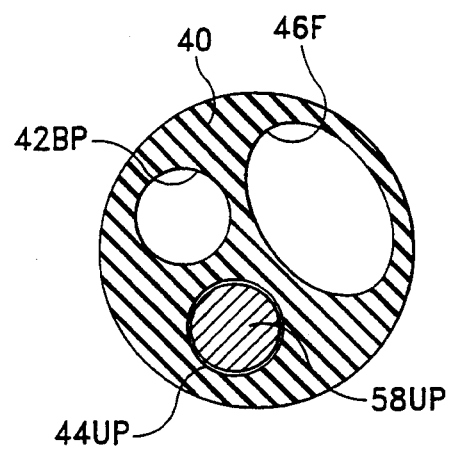
FIG. 4
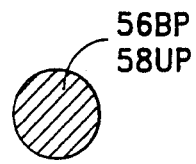
FIG. 5
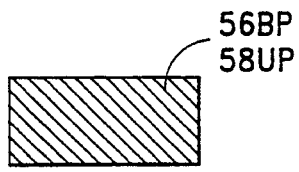
FIG. 6

5,385,563

URODYNAMIC CATHETER

BACKGROUND OF THE INVENTION

This invention relates to a catheter with multiple lumens for use in the dynamic monitoring of a urologic patient and, more particularly, to a urodynamic catheter having improved means for determining proper placement of the catheter for obtaining pressure profile readings of the bladder or of the bladder and urethra.

DESCRIPTION OF THE PRIOR ART

Need frequently arises to place a medico-surgical catheter within the urogenital tract of a male patient, or the urinary tract of a female patient, for purposes of treating, testing and monitoring the urologic patient.

These catheters, known in the art as urodynamic catheters, have at least a first pressure-sensing lumen provided with an opening to be positioned in the bladder in order to obtain pressure readings as the bladder is filled with liquid through a fill lumen of the catheter and then as the bladder empties when the patient voids.

Typically, urodynamic catheters will also have a second pressure-sensing lumen provided with an opening to be positioned in the urethra for pressure readings.

As will be appreciated, it is essential that the clinician be provided with means for determining whether the catheter is in fact positioned correctly within the urogenital tract, namely that, in a dual lumen catheter having only a first pressure-sensing lumen, the opening is within the bladder and that, in a triple lumen catheter having both first and second pressure-sensing lumens, the openings are positioned within the bladder and urethra, respectively.

A particularly efficacious means for determining proper positioning would be to utilize radio-opaque markers.

Such markers have heretofore been located on the circumference of the catheter tube. However, this then produces an outer surface of the catheter which is no longer smooth and moreover has enlarged surface areas where the markers are located, which in turn makes insertion of the catheter more uncomfortable and difficult.

Stated simply, the task of the present invention is to provide a urodynamic catheter wherein means are provided for ascertaining proper placement within the urogenital tract without adversely affecting the outer surface so as to render insertion more uncomfortable and difficult.

SUMMARY OF THE INVENTION

In accordance with this invention, the task is solved in an elegant manner by imbedding a radio-opaque element in each pressure-sensing lumen adjacent and distal to the lumen's opening through which the pressure is sensed.

The nature and objects of this invention will best be understood by reference to the following detailed description taken in conjunction with the accompanying illustrative drawings.

BRIEF DESCRIPTION OF THE DRAWINGS

FIG. 2 is an enlarged view of the separated distal end of the catheter shown in FIG. 1;

FIG. 3 is a sectional view of FIG. 2 taken along line 3—3;

FIG. 4 is a sectional view of FIG. 2 taken along line 4—4;

FIG. 5 is an end view of the radio-opaque marker shown in FIG. 3; and

FIG. 6 is a side view of the radio-opaque marker shown in FIG. 3.

DETAILED DESCRIPTION

Figure 1:
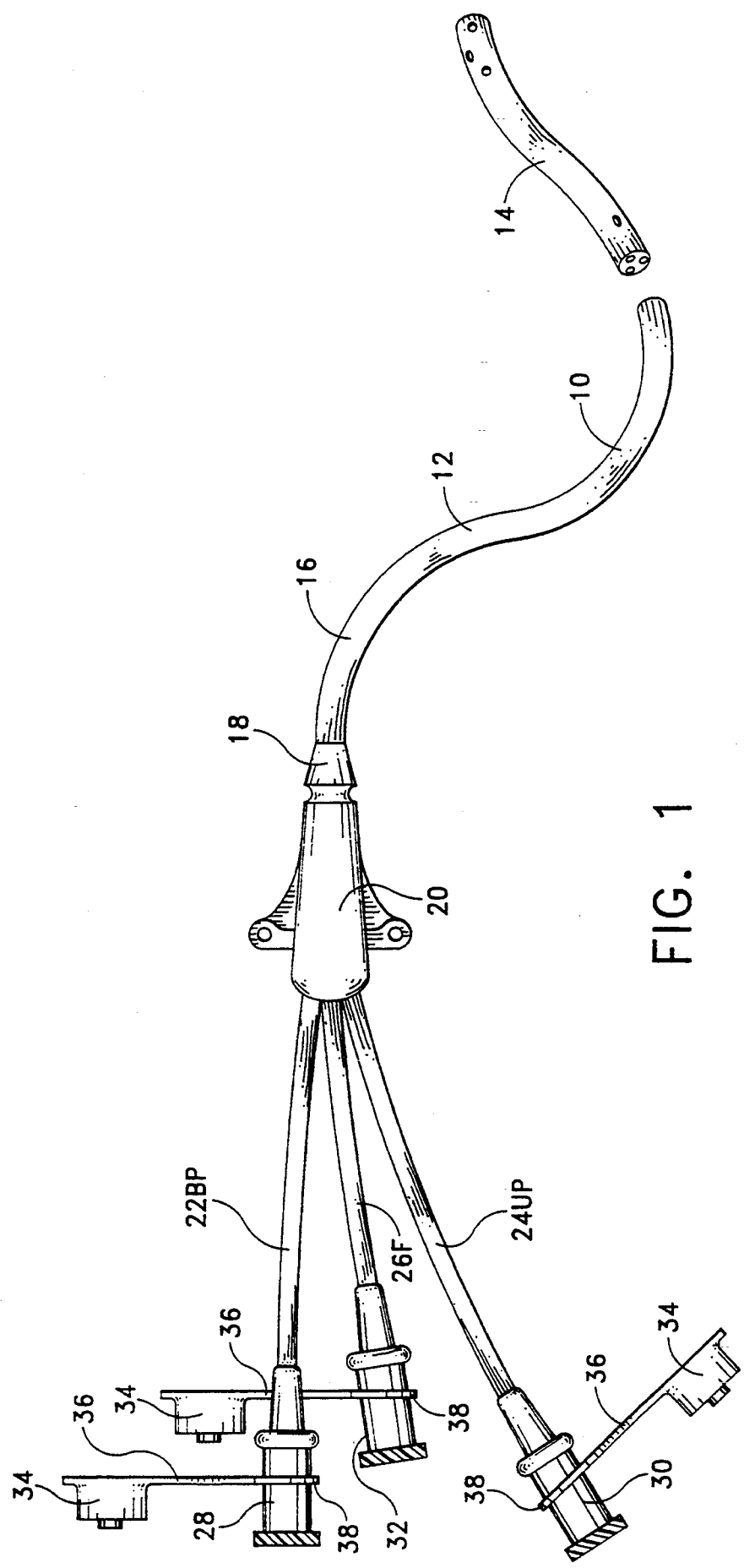
FIG. 1 is a side view of the urodynamic catheter of this invention with its distal end separated for purpose of illustration.

Referring to FIG. 1 there is shown the preferred embodiment of the urodynamic catheter of the present invention, generally designated as 10. The catheter 10 comprises an elongated tube 12 with a distal end 14 for insertion within the urogenital tract of a male patient, or the urinary tract of a female patient. The proximal end 16 of the tube 12 is secured to 18 for operating engagement with a manifold 20. The manifold has individual connection (not shown) to first, second and third extension tubings which for purposes of clarity are designated 22BP (BP=bladder pressure), 24UP (UP=urethra pressure) and 26F (F=fill), respectively.

As will be understood by those skilled in the art, in use, each of the pressure-sensing lumens 22BP and 24UP will be connected to a per se known device for sensing and recording pressure readings (not shown); and the fill lumen 26F will be connected in fluid communication with a source of liquid for filling the bladder in order to obtain the pressure readings. For this purpose, lumens 22BP, 24UP and 26F are provided at their proximal ends with luer connectors 28, 30 and 32 respectively, each having a cap 34 for sealing the openings in the connectors when not in use. As shown, each cap 34 is preferably secured to a connector by a linkage 36 and retainer ring 38.

Referring also to FIGS. 2–6, there is shown the catheter tube wall 40 which is made of flexible, imperforate material having first, second and third lumens 42BP, 44UP and 46F respectively therein. Each lumen 42BP, 44UP and 46F terminates internally within the distal end 14 and proceeds in an individual, unobstructed path proximally to tube connector 18 at the distal end of manifold 20 where lumens 42BP, 44UP and 46F are separately connected to extension tubings 22BP, 24UP and 26F, respectively, within the manifold 20.

With reference in particular to FIG. 2, the fill lumen 46F for discharging fluid into the bladder is preferably provided with two openings 48F and 50F extending through the tube wall 40 to fill the bladder; lumen 42BP has an opening 52BP situated between the fill lumens for sensing pressure in the bladder; and lumen 44UP has an opening 54UP located further upstream towards the proximal end of the catheter so as to be positioned within the urethra for pressure-sensing therein while opening 42BP is within the bladder.

While not critical to the practice of this invention, a typical 3-lumen urodynamic catheter may be on the order of about 35cm in length with the fill openings 48F, 50F approximately 0.5 cm and 1.5 cm, respectively, from the distal tip; opening 52BP substantially centrally disposed between fill openings 48F, 50F, i.e. on the order of 1.0 cm from the distal tip of the catheter; and opening 54UP approximately 11 cm from the distal tip.

The foregoing discussion is descriptive of an illustrative three-lumen urodynamic catheter of the prior art contemplated by the present invention. As such, it per se comprises no part of this invention.

The essence of the present invention is to provide radio-opaque markers in the form of inserts 56BP and 58UP situated within lumens 42BP and 44UP respectively, so as to visually identify, with an X-ray or other detector, the location of the pressure-sensing opening in the lumens 42BP and 44UP.

In order to do so, it will be appreciated that the inserts should be in close proximity with the openings 52BP and 54UP. Moreover, as seen in FIG. 6, the radio-opaque inserts should be downstream or distal to the associated opening in order not to impede pressure reading.

With reference to FIG. 4, the inserts are preferably in solid form conforming to the internal diameter of the lumen. However, it is also contemplated that they could be in the form of a tube having a central opening if so desired.

While the dimensions of the openings mentioned above for purposes of illustration are not critical, it will of course be appreciated that what is critical is that the distance between openings 42BP and 44UP must be predetermined such that the opening 44UP can be within the urethra while the openings 52BP and 50F are within the bladder.

It will be appreciated that various changes may be made without departing from the scope of the invention herein contemplated.

As already stated, the present invention also contemplates the 2-lumen urodynamic catheters, i.e. these having a single pressure-sensing lumen for sensing bladder pressure along with the requisite fill lumen.

The fill lumen has been shown to have two openings for passage of fluid through the catheter to the bladder. However, it is within the scope of the invention to have single opening which of necessity would be of larger diameter. Two (or more) openings are preferred in order to provide structural integrity to the catheter greater than that obtainable with a single larger opening.

As will be readily understood, in use the catheter is inserted in the patient and the clinician determines via a suitable detector device, e.g. an X-ray, radio, sound, magnetic resonance or cathode ray detector, the location of the radio-opaque markers with respect to the bladder or the bladder and urethra, as the case may be. Any necessary adjustments in positioning may then be made, the catheter secured in place and the medical procedures commenced.

It is to be understood that the above description and the accompanying drawings are merely illustrative of the preferred embodiment of the urodynamic catheter of the present invention, and that no limitations are intended other than as defined in the appended claims.

What is claimed is:

1. A urodynamic catheter comprising a flexible tube having a distal end for insertion within the urogenital tract of a male patient or the urinary tract of a female patient and an opposed proximal end;
   a fill lumen extending between the ends of the tube and having at least one opening at its distal end adapted for introducing a liquid into a patient's bladder;
   a first pressure-sensing lumen having an opening adapted for being positioned within the bladder for obtaining pressure readings as the bladder is filled with liquid through the fill lumen and then as the bladder empties; and
   a radio-opaque marker element fixedly seated within the first pressure-sensing lumen in close proximity and distal to the opening in the pressure-sensing lumen.

2. A urodynamic catheter as defined in claim 1 wherein the fill lumen has a pair of openings for introducing a liquid into the bladder.

3. A urodynamic catheter as defined in claim 2 wherein the opening in the first pressure-sensing lumen is disposed longitudinally between the pair of openings in the fill lumen.

4. A urodynamic catheter as defined in claim 1 including a second pressure-sensing lumen having an opening adapted to be positioned within a patient's urethra for obtaining pressure readings of the urethra while the openings in the fill lumen and first pressure-sensitive lumens remain positioned in the bladder; and a radio-opaque marker element fixedly seated within the second pressure-sensing lumen in close proximity and distal to the opening in the second pressure-sensing lumen.

5. A urodynamic catheter as defined in claim 4 wherein the proximal end of each pressure-sensing lumen is adapted for connection to means for determining pressure readings; and the proximal end of the fill lumen is adapted for placement in fluid communication with a source of liquid for filling the bladder.

6. A urodynamic catheter comprising a flexible tube having opposed proximal and distal ends, the distal end being adapted for insertion within the urogenital tract of a male patient or the urinary tract of a female patient;
   a fill lumen extending between the ends of the tube and having at least one opening at its distal end adapted for introducing a liquid into a patient's bladder in preparation for obtaining pressure profile readings of the bladder and the urethra;
   a first pressure sensing lumen extending between the ends of the tube and having an opening adapted for being positioned within the bladder for obtaining pressure readings as the bladder is filled with liquid through the fill lumen and then as the bladder empties, the first pressure-sensing lumen having a radio-opaque marker element fixedly seated therein in close proximity and distal to the opening in the first pressure-sensing lumen;
   and a second pressure-sensing lumen extending between the ends of the tube and having an opening positioned proximal to the opening in the first pressure-sensitive lumen such that when the openings in the first pressure-sensing lumen and fill lumen are positioned within the bladder the opening in the second pressure-sensing lumen can be positioned within the patient's urethra, the second pressure-sensing lumen having a radio-opaque marker element in close proximity to and distal to the opening in the second pressure-sensing lumen,
   whereby the precise-location of the urodynamic catheter inserted in the patient can be determined by detector means determining the location of the radio-opaque elements with respect to the bladder and urethra, respectively, and any necessary positioning adjustments made to place the first and second pressure-sensing lumens in proper positioning for obtaining pressure readings of the bladder and urethra.

* * * * *